United States Patent
Lee et al.

(10) Patent No.: US 9,552,153 B2
(45) Date of Patent: Jan. 24, 2017

(54) ULTRASOUND APPARATUS AND METHOD OF INPUTTING INFORMATION INTO THE SAME

(71) Applicant: SAMSUNG MEDISON CO., LTD., Hongcheon-gun, Gangwon-do (KR)

(72) Inventors: Yun-hee Lee, Gangwon-do (KR); Seung-ju Lee, Gangwon-do (KR); Tae-hun Kim, Gangwon-do (KR)

(73) Assignee: SAMSUNG MEDISON CO., LTD., Hongcheon-gun, Gangwon-Do (KR)

( * ) Notice: Subject to any disclaimer, the term of this patent is extended or adjusted under 35 U.S.C. 154(b) by 209 days.

(21) Appl. No.: 14/096,925

(22) Filed: Dec. 4, 2013

(65) Prior Publication Data
US 2014/0164997 A1   Jun. 12, 2014

(30) Foreign Application Priority Data

Dec. 12, 2012 (KR) .................. 10-2012-0144661
Oct. 4, 2013 (KR) .................. 10-2013-0118735

(51) Int. Cl.
*G06F 3/0484* (2013.01)
*G06F 3/0488* (2013.01)
*A61B 8/00* (2006.01)

(52) U.S. Cl.
CPC .......... *G06F 3/0488* (2013.01); *A61B 8/4405* (2013.01); *A61B 8/461* (2013.01); *A61B 8/465* (2013.01); *A61B 8/467* (2013.01); *G06F 3/04847* (2013.01); *G06F 3/04883* (2013.01); *G06F 3/04886* (2013.01); *G06F 2203/04808* (2013.01)

(58) Field of Classification Search
CPC .. G06F 3/04842; G06F 3/0488; G06F 3/0482; G06F 2203/04808; A61B 8/00; A61B 8/461; A61B 8/465
See application file for complete search history.

(56) References Cited

U.S. PATENT DOCUMENTS 6,468,212 B1   10/2002   Scott et al.
6,599,244 B1*   7/2003   Epps .................. A61B 8/00
                                                              600/437
(Continued)

FOREIGN PATENT DOCUMENTS

EP   2191776 A1   6/2010
JP   6-30938 A   2/1994
(Continued)

OTHER PUBLICATIONS

Extended European Search Report issued in European Application No. 13192401.1-1660 dated Mar. 20, 2014.
(Continued)

*Primary Examiner* — Anil Bhargava
(74) *Attorney, Agent, or Firm* — McDermott Will & Emery LLP

(57) ABSTRACT

Provided are an ultrasound apparatus and a method of inputting information into the ultrasound apparatus. The method includes receiving a selection of a control item of the ultrasound apparatus from a user via a control area included in the user input unit; displaying a control window for displaying the selected control item on a screen; adjusting a configuration value of the selected control item based on a touch operation of a touch input which is received via the control area.

33 Claims, 15 Drawing Sheets

(56) References Cited

U.S. PATENT DOCUMENTS

| | | |
|---|---|---|
| 6,638,223 B2 | 10/2003 | Lifshitz et al. |
| 2007/0191380 A1 | 8/2007 | Ding et al. |
| 2008/0094367 A1 | 4/2008 | Van De Ven et al. |
| 2009/0043195 A1* | 2/2009 | Poland ............... A61B 8/00 600/437 |
| 2009/0153495 A1* | 6/2009 | Chen ............... G06F 3/04847 345/173 |
| 2010/0004539 A1* | 1/2010 | Chen ............... A61B 8/0825 600/445 |
| 2010/0049046 A1* | 2/2010 | Peiffer ............... A61B 8/13 600/443 |
| 2010/0145195 A1* | 6/2010 | Hyun ............... A61B 8/00 600/437 |
| 2010/0321324 A1 | 12/2010 | Fukai et al. |
| 2011/0043434 A1 | 2/2011 | Roncalez et al. |
| 2012/0056837 A1* | 3/2012 | Park ............... G06F 3/0414 345/173 |
| 2012/0123627 A1 | 5/2012 | Sourioux et al. |
| 2013/0072795 A1* | 3/2013 | Mo ............... A61B 8/465 600/443 |
| 2014/0046185 A1* | 2/2014 | Mo ............... A61B 8/467 600/443 |

FOREIGN PATENT DOCUMENTS

| | | |
|---|---|---|
| JP | 2003-10182 A | 1/2003 |
| JP | 2013-102805 A | 5/2013 |
| KR | 2010-0065720 A | 6/2010 |
| KR | 10-1194294 B1 | 10/2012 |

OTHER PUBLICATIONS

Korean Notice of Allowance issued in Korean Application No. 10-2013-0118735 dated Mar. 31, 2015, with English Translation.

Korean Office Action issued in Application No. 10-2013-0118735 dated Dec. 23, 2014, with English Translation.

\* cited by examiner

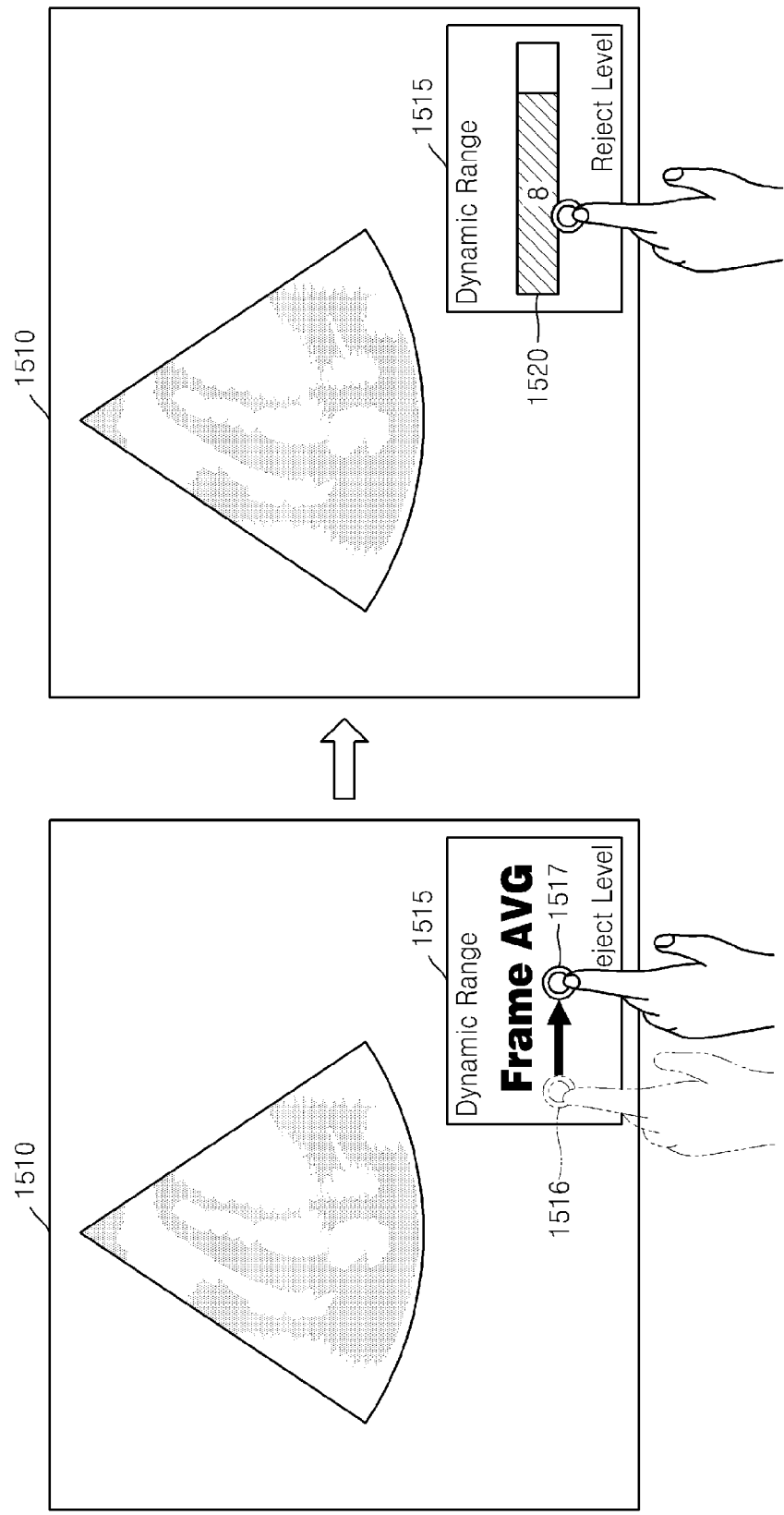

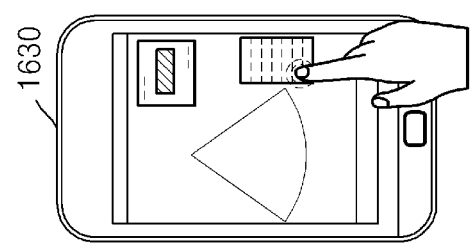
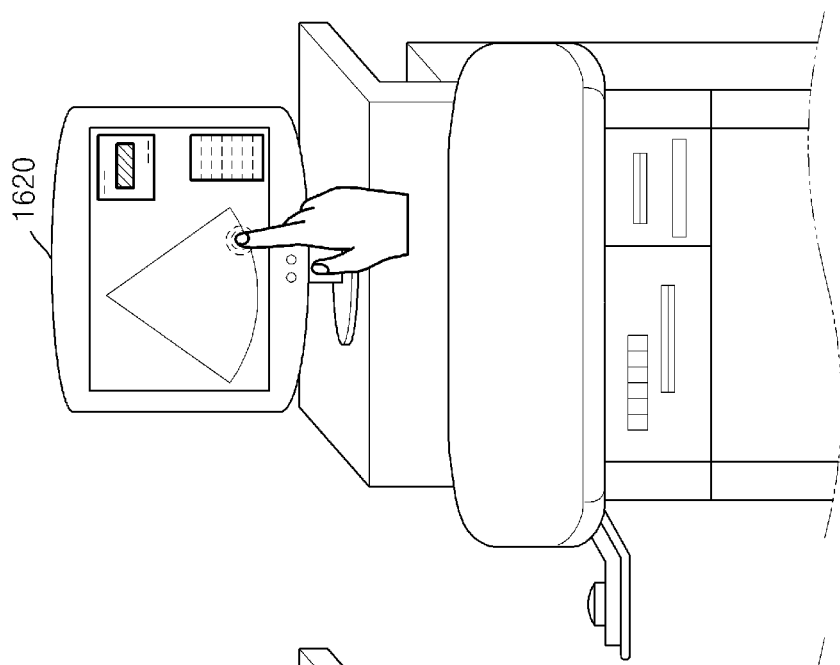
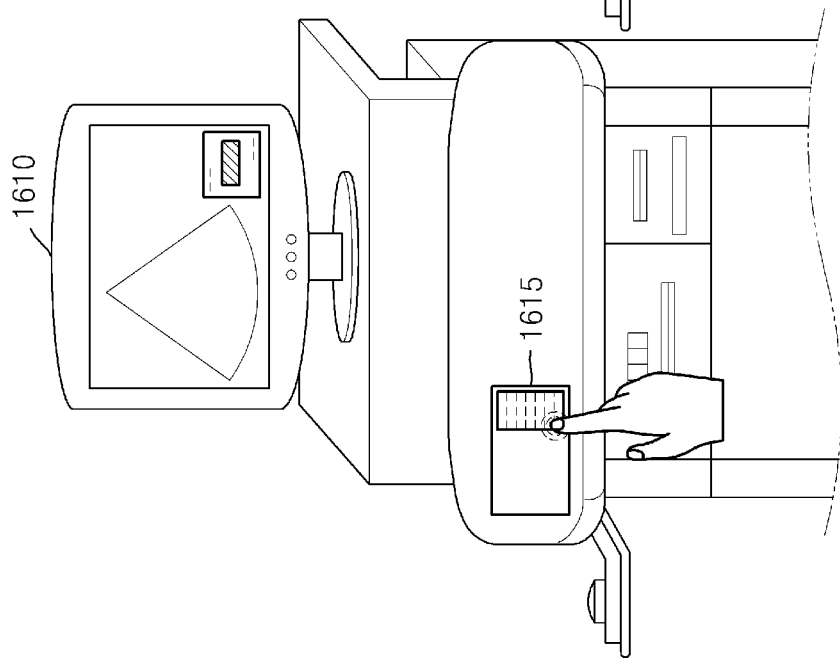

ULTRASOUND APPARATUS AND METHOD OF INPUTTING INFORMATION INTO THE SAME

RELATED APPLICATIONS

This application claims the benefit of Korean Patent Application No. 10-2012-0144661, filed on Dec. 12, 2012, in the Korean Intellectual Property Office, and Korean Patent Application No. 10-2013-0118735, filed on Oct. 4, 2013, in the Korean Intellectual Property Office, the disclosure of which is incorporated herein in its entirety by reference.

BACKGROUND

1. Field

One or more embodiments of the present invention relate to an ultrasound apparatus that is capable of receiving a touch input and a method of inputting information into the ultrasound apparatus.

2. Description of the Related Art

A probe of an ultrasound apparatus is placed in closed contact with a predetermined portion in a body and generates an ultrasound signal having a frequency of 20 kHz or higher. Then, the ultrasound apparatus obtains an image of the predetermined portion via information about the characteristics of a reflected echo signal. Such ultrasound apparatus is used for medical purposes such as detection of foreign objects inside a body, injury diagnosis, treatment observation, etc. The ultrasound apparatus has higher stability compared to an X-ray apparatus and may display an image in real time. Additionally, a patient is not exposed to radiation when the ultrasound apparatus is used. Therefore, the ultrasound apparatus is widely used, along with an X-ray diagnosis apparatus, a computerized tomography (CT) apparatus, a magnetic resonance image (MRI) apparatus, a nuclear medicine diagnosis apparatus, or other image diagnosis apparatuses.

Parameters for obtaining an image of an organ by using an ultrasound apparatus are generally set. However, the characteristics of an ultrasound signal reflected from an organ may vary with the characteristics of the organ. Thus, in order to obtain an accurate image for diagnosing a body organ, it is necessary to allow a user to properly adjust parameters of the ultrasound apparatus.

SUMMARY

Additional aspects will be set forth in part in the description which follows and, in part, will be apparent from the description, or may be learned by practice of the presented embodiments.

According to one or more embodiments of the present invention, a method of inputting information into an ultrasound apparatus that includes a user input unit for receiving a touch input, the method includes receiving a selection of a control item of the ultrasound apparatus from a user via a control area included in the user input unit; displaying a control window for displaying the selected control item on a screen; and adjusting a configuration value of the selected control item based on a touch operation of a touch input which is received via the control area.

The control item may include a plurality of parameters regarding an ultrasound image, and wherein the plurality of parameters matches a plurality of areas which are arranged in the control area.

The displaying may include displaying the selected control item and another control item that is arranged adjacent to the selected control item in the control window.

The receiving of the selection may include detecting a location of a touch input to the control area of the user; and obtaining a control item which corresponds to the detected location.

The method of inputting information into the ultrasound apparatus may further include displaying the adjusted configuration value in the control window.

The touch operation may include at least one of a pressure operation for changing a pressure of the touch input and a location operation for changing a location of the touch input.

When the touch operation includes the pressure operation, the adjusting of the configuration value may include increasing or decreasing the configuration value in a direction in which a pressure of the touch input to the control area increases.

The direction in which the pressure increases may be determined based on a center of the touch input.

When the touch operation increases the location operation, the adjusting of the configuration value may include increasing or decreasing the configuration value in a direction in which a location of the touch input to the control area is changed.

The direction in which the location is changed may be a direction in which the touch input is dragged.

The plurality of areas may be arranged in at least one from among a horizontal direction of the control area, a vertical direction of the control area, a circle pattern, and a grid pattern.

The receiving of the selection may include detecting a touch input of the user to the control area; and obtaining the control item that corresponds to a predetermined location in the control area.

The predetermined location may be determined based on at least one of a frequency in which a control item is selected and a user input.

The adjusting may include adjusting the configuration value based on acceleration of the touch input for changing the touch input.

The control item may include at least one parameter from among a frequency of an ultrasound signal, a dynamic range, a frame average, a reject level, a power, a filter, and a line density, the parameter being related to an operation of the ultrasound apparatus.

The control item may include at least one parameter from among color, brightness, a chroma, sharpness, contrast, and resolution, the parameter being related to an image output of the ultrasound apparatus.

The user input unit may be at least one of a touch screen, a touch panel, and a touch pad.

According to one or more embodiments of the present invention, an ultrasound apparatus includes: an obtaining unit for obtaining ultrasound data from an object; a user input unit that includes a control area and receives a selection of a control item of the ultrasound apparatus from a user via the control area; a display unit for displaying an ultrasound image based on the ultrasound data, and displaying a control window which shows the selected control item; and a control unit for adjusting a configuration value of the selected control item based on a touch operation of a touch input which is received via the control area.

According to one or more embodiments of the present invention, a method of inputting information into an ultrasound apparatus that includes a user input unit for receiving a touch input, the method includes: receiving a selection of a control item of the ultrasound apparatus from a user via a control area included in the user input unit; displaying a control window for displaying the selected control item on a screen; and adjusting a configuration value of the selected control item based on a touch operation of a touch input which is received via the control area.

According to another aspect of the present invention, there is provided a non-transitory computer-readable storage medium having stored thereon a computer program, which when executed by a computer, performs the method.

BRIEF DESCRIPTION OF THE DRAWINGS

These and/or other aspects will become apparent and more readily appreciated from the following description of the embodiments, taken in conjunction with the accompanying drawings in which:

FIG. 15 is a diagram for explaining an embodiment in which a touch input is detected via a control window; and FIGS. 16A through 16C are diagrams for explaining several methods of receiving a touch input, according to an embodiment of the present invention.

DETAILED DESCRIPTION

Figure 1:
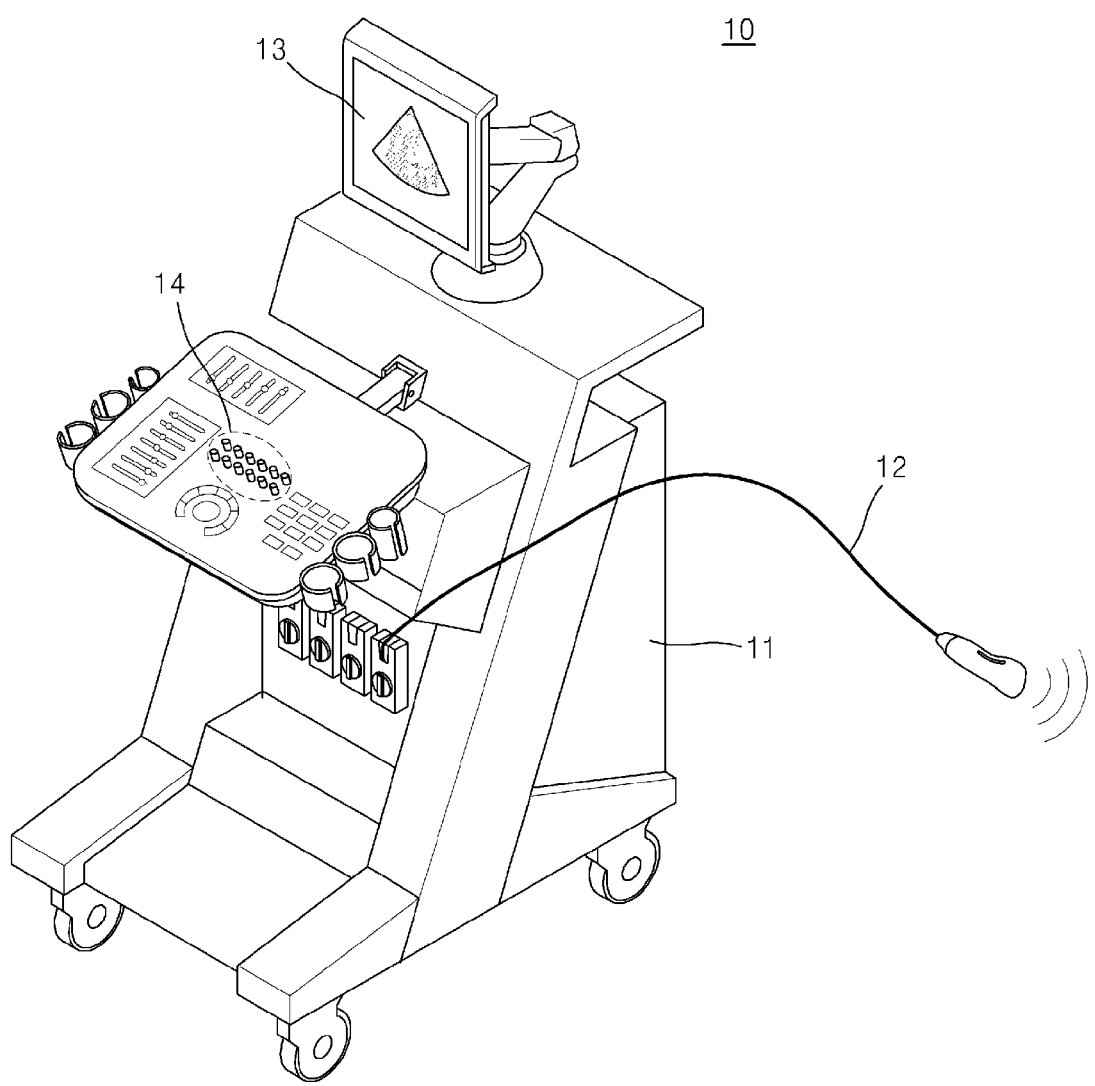
FIG. 1 is a diagram illustrating an ultrasound system for diagnosing an organ.

General and widely-used terms that have been employed herein in consideration of the functions provided in the present invention may vary according to the intention of one of ordinary skill in the art, case precedents, or the occurrence of new technologies. Additionally, in some cases, an applicant may arbitrarily select specific terms. Then, the applicant will provide the meaning of the terms in the description of the present invention. Accordingly, it will be understood that the terms used herein should be interpreted as having a meaning that is consistent with the context of the relevant art and will not be interpreted in an idealized or overly formal sense unless expressly so defined herein.

It will be further understood that the terms "comprises," "comprising," "includes," and/or "including," when used herein, specify the presence of components, but do not preclude the presence or addition of one or more other components, unless otherwise specified. Additionally, terms used herein, such as 'unit' or 'module', mean entities for processing at least one function or operation. These entities may be implemented by hardware, software, or a combination of hardware and software.

In the description of the present invention, an "ultrasound image" is an image of an object which is obtained by using an ultrasound signal. An object may mean a part of a physical body. For example, the object may be an organ such as the liver, heart, nuchal translucency (NT), brain, breast, or abdomen, a fetus, etc.

An ultrasound image may be of various types. For example, an ultrasound image may be at least one of an amplitude (A) mode image, a brightness (B) mode image, a color (C) mode, and a doppler (D) mode. Additionally, according to an embodiment of the present invention, an ultrasound image may be a two-dimensional (2D) image or a three-dimensional (3D) image.

A "user", as presented in the description of the present invention, may be a medical expert such as a medic, a nurse, a medical laboratory technologist, or a sonographer, but is not limited thereto.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

FIG. 1 is a diagram illustrating an ultrasound system 10 for diagnosing an object by using an ultrasound signal. According to an embodiment of the present invention, the ultrasound system 10 includes a main body 11, one or more probes 12, a display unit 13, and a control panel.

A user places the probe 12, which transmits an ultrasound signal, near an object, and obtains ultrasound data from an echo signal received from the object. Then, the user may diagnose the object by using an ultrasound image which is created by analyzing the ultrasound data and displayed on the display unit 13. The control panel in the current embodiment may include one or more parameter adjustment units 14 for controlling a parameter of an ultrasound apparatus. The parameter adjustment unit 14 may include one or more knob buttons.

The user of the ultrasound system 10 controls an operation of the ultrasound apparatus by using the parameter adjustment unit 14 which is provided as a hardware device on the control panel. Accordingly, the user may easily use a frequently used parameter by memorizing a physical location of the parameter. However, the user may sometimes not look at the control panel while diagnosing an object. Additionally, the user may manually manipulate the parameter adjustment unit 14 in order to adjust a parameter of the ultrasound apparatus. Thus, work efficiency may deteriorate.

Accordingly, a method and an apparatus for diagnosing an object by adjusting a parameter of the ultrasound apparatus while a user is constantly looking at the display unit 13 is necessary.

Figure 2:
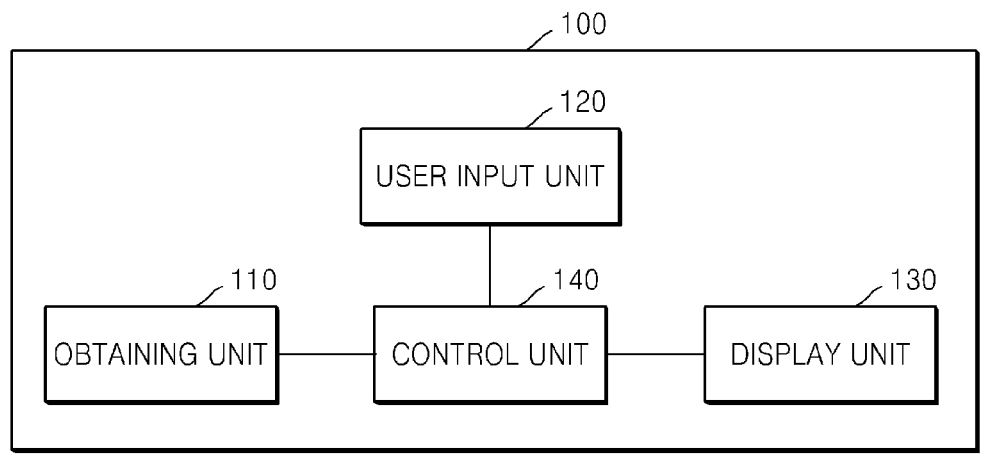
FIG. 2 is a block diagram illustrating an ultrasound apparatus according to an embodiment of the present invention.

FIG. 2 is a block diagram illustrating an ultrasound apparatus 100 according to an embodiment of the present invention. The ultrasound apparatus 100, in the current embodiment, may include an obtaining unit 110, a user input unit 120, a display unit 130, and a control unit 140. In addition to units shown in FIG. 1, the ultrasound apparatus 100 may further include other general-use elements.

The ultrasound apparatus 100, according to an embodiment of the present invention, is an apparatus that may obtain ultrasound data from an object by using an ultrasound wave and provide a user with a graphic user interface (GUI) for adjusting a parameter of the ultrasound apparatus 100.

The ultrasound apparatus 100, according to an embodiment of the present invention, may be implemented in various forms. For example, the ultrasound apparatus 100 may be a mobile terminal or a fixed terminal. An example of a mobile terminal may include a picture archiving and communication system (PACS) viewer, a smart phone, a laptop computer, a personal digital assistant (PDA), a tablet personal computer (PC), and so on.

Hereinafter, elements included in the ultrasound apparatus 100 are described.

The obtaining unit 110 obtains ultrasound data regarding an object. The ultrasound data in the current embodiment may be two-dimensional (2D) data or three-dimensional (3D) data regarding the object. Additionally, the ultrasound data may include doppler data which is data representing a motion of the object.

According to an embodiment of the present invention, the obtaining unit 110 may include a probe (not illustrated) for transmitting and receiving an ultrasound signal, and a beam former (not illustrated) for transmission and reception convergence of an ultrasound signal. According to an embodiment of the present invention, the probe may include at least one of a one-dimensional (1D) probe, a 1.5D probe, a 2D matrix probe, and a 3D probe.

As described above, the obtaining unit 110 may scan an object by transmitting and receiving an ultrasound signal, thus directly obtaining ultrasound data. Additionally, the obtaining unit 110 may obtain pre-obtained ultrasound data from another device or an external server.

That is, the obtaining unit 110 may receive ultrasound data in a wired or wireless manner, by using one or more element that allows communication with the ultrasound apparatus 100 and an external apparatus. For example, the obtaining unit 110 may obtain ultrasound data by using a near field communication (NFC) module, a mobile communication module, a wireless internet module, and a wired internet module.

The NFC module is a module for NFC. A wireless local area network (LAN) which is a Wi-Fi, Bluetooth (BLE), ultra wideband (UWB), Zigbee, NFC (Near Field Communication), Wi-Fi direct (WFD), or infrared data association (IrDA) network may be employed as NFC technology.

The mobile communication module transmits and receives a wireless signal to and from with at least one of a base station, an external terminal, and a server on a mobile communication network. The wireless Internet module is a module for wireless internet access. The wireless Internet module is built inside or outside the obtaining unit 110. The wired Internet module is a module for wired Internet access.

According to an embodiment of the present invention, the obtaining unit 110 may receive ultrasound data from an external apparatus through wired or wireless communication. An external apparatus, according to an embodiment of the present invention, may be a cellular phone, a smart phone, a laptop computer, a tablet PC, an e-book terminal, a digital broadcasting terminal, a PDA, a portable multimedia player (PMP), or a digital camera, but is not limited thereto.

The obtaining unit 110 may obtain ultrasound data in a wired or wireless manner from a hospital server or a cloud server through a PACS, as well as through the external device.

The user input unit 120 is an element for inputting information and data which are used by a user to control the ultrasound apparatus 100. The user input unit 120 may receive various types of control inputs from a user. For example, the user input unit 120 may receive a touch input.

The user input unit 120 may be a key pad, a track ball, a mouse, a dome switch, a touch pad, which may be a capacitive overlay type, a resistive overlay type, an infrared beam type, a surface acoustic wave type, an integral strain gauge type, or a piezo electric type, a touch panel, a jog wheel, or a jog switch, but is not limited thereto. Particularly, the user input unit 120 may also include a touch screen in which a touch pad and the display unit 130, which will be described later, form a layered structure.

A touch screen may detect a proximity touch, as well as a real touch. The real touch in the description of the present invention is a touch of a pointer on a screen. The proximity touch is a touch of a pointer that only approaches a screen at a predetermined distance. The pointer in the description of the present invention is a tool for touching or proximately touching a particular portion of a displayed screen. An example of the pointer may be a stylus pen or a finger.

Though not illustrated in the drawing, various types of sensors may be disposed inside or near the touch screen, in order to detect a touch or a proximity touch on the touch screen. An example of a sensor for detecting a touch on the touch screen may be a tactile sensor. The tactile sensor is a sensor for detecting a contact of a specific object to such a degree that humans may feel it or to a higher degree. The tactile sensor may detect various types of information such as information about a roughness of a contact surface, a hardness of a contact object, or a temperature at a contact point.

Additionally, an example of a sensor for detecting a touch on the touch screen is a proximity sensor. The proximity sensor is a sensor for detecting an object which is approaching a predetermined detection surface or detecting a neighboring object by using the strength of an electromagnetic field or an infrared light without a mechanical contact. Examples of the proximity sensor include a transmission-type photoelectric sensor, a direct reflection-type photoelectric sensor, a mirror reflection-type photoelectric sensor, a high-frequency oscillation proximity sensor, an electrostatic capacity-type proximity sensor, a magnetic-type proximity sensor, and an infrared proximity sensor.

The user input unit 120 may receive various forms of touch input from the user. A user input detected by the user input unit 120 may include a tap, a touch and hold, a double-tap, a drag, panning, a flick, a drag-and-drop, a swipe, pinching, unpinching, tilting, and so on. Additionally, the user input may include a one-point input and a two-point input, a three-point input, and a four-point for four or more touch inputs according to the number of detected inputs. Each user input is described with reference to particular embodiments.

Additionally, the user input unit 120 may detect a touch operation corresponding to a received touch input based on various sensors as described above. Examples of a touch operation may include a pressure operation for changing a pressure of a touch input and a location operation for changing a location of a touch input. Furthermore, the user input unit 120 may detect an acceleration by which a touch operation changes, and may measure an acceleration by which a pressure or a location changes in time.

The display unit 130 displays and outputs information processed by the ultrasound apparatus 100. For example, the display unit 130 may display an ultrasound image of an object on a screen, or display a user interface (UI) or a graphic user interface (GUI) which is related to a functional setting.

The display unit 130 may include at least one from among a liquid crystal display (LCD), a thin-film transistor-liquid crystal display (TFT-LCD), an organic light-emitting diode (OLED), a flexible display, a 3D display, and an electrophoretic display. According to an exemplary embodiment, the ultrasound apparatus 100 may include two or more display units 130.

If the display unit 130 and the user input unit 120 described above form a layered structure to constitute a touch screen, the display unit 130 may be also used as an input device as well as an output device.

The control unit 140 controls all operations of the ultrasound apparatus 100. That is, the control unit 140 may control all operations of the obtaining unit 110, the user input unit 120, and the display unit 130.

Figure 3:
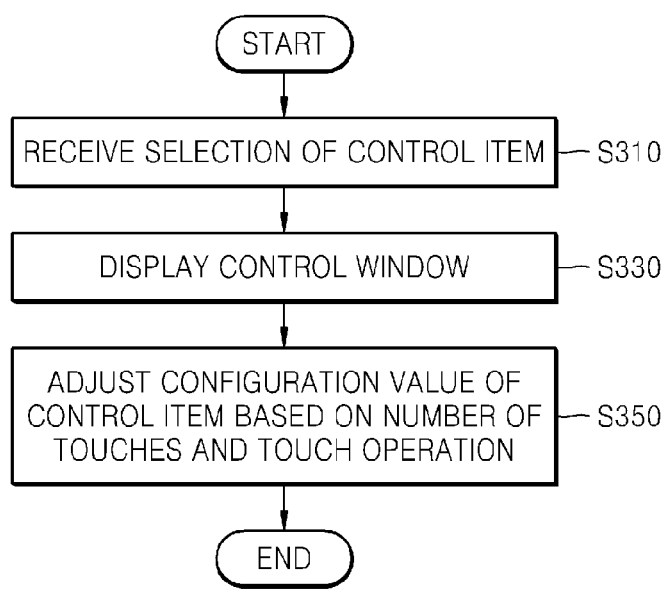
FIG. 3 is a flowchart for explaining a method of inputting information into an ultrasound apparatus, according to an embodiment of the present invention.

Hereinafter, a method of inputting information by using a touch input by using the elements included in the ultrasound apparatus 100 will be described with reference to FIG. 3. FIG. 3 is a flowchart for explaining a method of inputting information, according to an embodiment of the present invention. The flowchart shown in FIG. 3 includes operations processed in time series by using the ultrasound apparatus 100, the obtaining unit 110, the user input unit 120, the display unit 130, and the control unit 140. Therefore, even if omitted below, the description given above with respect to the units shown in FIG. 2 may also be applied to the flowchart shown in FIG. 3.

In operation S310, the ultrasound apparatus 100 receives a user input for selecting a control item from a user. That is, the ultrasound apparatus 100 may receive a selection of a control item from the user via the user input unit 120.

A control item means a plurality of parameters regarding the ultrasound apparatus 100. That is, a control item may include a plurality of parameters regarding an operation or an image output of the ultrasound apparatus 100.

Specifically, examples of control items related to an operation of the ultrasound apparatus 100 may include parameters such as a frequency of an ultrasound signal, a dynamic range, a frame average, a reject level, a power, a filter, and a line density. Examples of control items regarding an image output of the ultrasound apparatus 100 may include parameters such as color, brightness, chroma, sharpness, contrast, and resolution. Control items related to the ultrasound apparatus 100 may further include various types of parameters, in addition to the parameters described above.

In operation S310, the ultrasound apparatus 100 may receive a user input for selecting a control item via a control area of the user input unit 120. A control area is an area of the user input unit 120 which matches a control item that is a parameter of the ultrasound apparatus 100 as described above. That is, in operation S310, the ultrasound apparatus 100 may detect a location of a user input which is received via the control area, thereby obtaining a control item that matches the corresponding location. The control area may be an entire or a partial area included in the user input unit. The control area will be described specifically in FIG. 4.

A touch input by a user received by the ultrasound apparatus 100 in operation S310 may be a tap input and/or a drag input which is detected in a control area. For example, a user may tap a location in the control area or drag a specific location in the control area.

A "tap" is a gesture by which a user touches a screen by using a finger or a touch tool, for example, an electronic pen, and then, immediately lifts it off from the screen without dragging on the screen. A "drag" is a gesture by which a user touches a screen by using a finger or a touch tool and moves the finger or the touch tool to another location on the screen while holding the touch.

According to an embodiment of the present invention, in operation S310, the ultrasound apparatus 100 may obtain a control item that corresponds to a predetermined location. In other words, the ultrasound apparatus 100 may obtain a control item, which corresponds to a location that is pre-stored in the ultrasound apparatus 100, regardless of a location in a control area of a touch input. A touch input by a user may be employed as a signal for obtaining, performed by the ultrasound apparatus 100, a control item, regardless of a location of the touch input. With regard to the current embodiment, this will be described in detail in FIG. 14.

In operation S330, the ultrasound apparatus 100 displays a control window. That is, the ultrasound apparatus 100 may display a control window for showing a control item selected in operation S310 via the display unit 130.

The control window may be a UI or GUI for visually outputting a control item via the display unit 130. That is, the ultrasound apparatus 100 may display a control window for showing the control item selected in operation S310 on a screen of the display unit 130 by using various methods. For example, the ultrasound apparatus 100 may display a control window by using at least one of graphic data and text data, or by using an on-screen display (OSD) or an on-screen graphic (OSG).

According to an embodiment of the present invention, the ultrasound apparatus 100 may display one or more other control items in the control window, as well as the control item selected in operation S310. A relevant embodiment will be described again with respect to FIG. 5.

Referring to FIGS. 5 through 9, the ultrasound apparatus 100 displays a control window in a lower right part of the display unit 130. This will be described later. However, a location of a control window is not limited thereto. That is, the ultrasound apparatus 100 may display a control window in various locations of the display unit 130. The ultrasound apparatus 100 may also display a control window to overlap with an ultrasound image.

In operation S330, when the ultrasound apparatus 100 displays the control window, the user may identify the currently selected control item, and thus, may control a parameter of the ultrasound apparatus 100.

In operation S350, the ultrasound apparatus 100 adjusts a configuration value of the control item, based on a touch input. That is, the ultrasound apparatus 100 may receive a touch input, for adjusting a parameter of the ultrasound apparatus 100, from the user. Then, the ultrasound apparatus 100 may increase or decrease a configuration value of a parameter for the control item which is selected in operation S310, based on the touch input.

In detail, in operation S350, the ultrasound apparatus 100 may adjust a configuration value of a control item, based on a touch operation of a touch input. According to an embodiment of the present invention, the ultrasound apparatus 100 may adjust a configuration value based on a number of touches and a touch operation of a touch input. Additionally, the ultrasound apparatus 100 may also adjust a configuration value based on a pressure operation and a location operation as described with reference to FIG. 1. Embodiments, in which the ultrasound apparatus 100 adjusts a configuration value according to various types of touch inputs, will be described with reference to FIGS. 5 through 9.

The touch input in operation S350 may be received via the control area described in operation S310. That is, a touch input for selecting a control item in operation S310 is described separately from a touch input for adjusting a configuration value in operation S350. However, the ultrasound apparatus 100 may sequentially receive two inputs via the control area. A detailed description about adjusting a configuration value according to a touch input will be specifically described with reference to FIGS. 5 through 9. According to another embodiment of the present invention, in operation S350, a touch input may be received via the control window, which was described with regard to operation S330. This will be described by referring to FIG. 15.

Though not illustrated in FIG. 3, a method of inputting information into the ultrasound apparatus in the current embodiment, may further include displaying an adjusted configuration value after operation S350 is performed. That is, in operation S350, the ultrasound apparatus 100 may adjust a configuration value based on a touch input and output the adjusted configuration value as visual information. Thus, the ultrasound apparatus 100 may immediately provide the user with a change in a parameter of the ultrasound apparatus 100. Such an embodiment will be described with reference to FIGS. 7 and 9.

According to the method of inputting information described in FIG. 3, the user of the ultrasound apparatus 100 may easily adjust a parameter of the ultrasound apparatus 100 via the user input unit 130 without having to identify a location of a hardware device. Accordingly, the user may manipulate the ultrasound apparatus 100 while looking at an ultrasound image of the object, and identify a result of the manipulation. Thus, the time for diagnosing an object may be shortened and image accuracy may also be improved.

Figure 4:
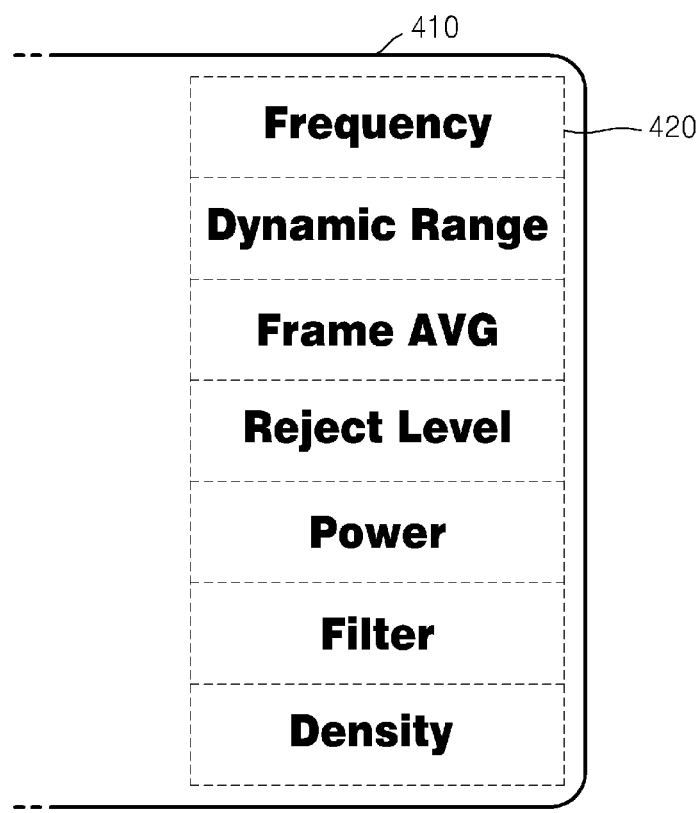
FIG. 4 is a diagram illustrating a plurality of parameters which match a user input unit, according to an embodiment of the present invention.

FIG. 4 is a diagram illustrating a plurality of parameters which match a user input unit 410, according to an embodiment of the present invention. FIG. 4 illustrates the user input unit 410 and a control area 420 which is a partial area of the user input unit 410. That is, the ultrasound apparatus 100 may receive a user input for selecting a control item from a user via the control area 420 which is shown in a dotted line. As illustrated in FIG. 4, the control area 420 may be implemented as a partial area of the user input unit 410 or an entire area of the user input unit 410.

Referring to FIG. 4, the control items include a frequency of an ultrasound signal, a dynamic range, a frame average, a reject level, a power, a filter, and a line density. However, the control items that match the control area 420 are not limited thereto. That is, the control items may include various parameters of the ultrasound apparatus 100, as described above.

The control items respectively match a plurality of areas in the control area 420. That is, seven parameters, shown in FIG. 4, may match the control area 420 which is divided into seven areas. The seven areas divided from the control area 420 are arranged along an axis of the control area 420. FIG. 4 shows the seven areas are arranged in a vertical direction. However, an arrangement of the seven areas is not limited thereto, and the seven areas may be arranged in a horizontal direction. Embodiments, with regard to types of arrangement in the control area 420, will be described later in detail in FIGS. 11 through 13.

According to an embodiment of the present invention, the number of divided areas may be determined according to the number of parameters included in a control item. The ultrasound apparatus 100 may divide the control area 420, according to the number of parameters selected by a user or determined according to the system. Then, the ultrasound apparatus 100 may match and store parameters in respective divided areas of the control area 420.

If a touch input to the control area 420 from the user is detected, the ultrasound apparatus 100 obtains a control item which corresponds to the detected touch input. That is, the ultrasound apparatus 100 may detect a location of the touch input, and select a control item which matches the detected location and is pre-stored. For example, if the user touches an uppermost area of the control area 420 from among the seven divided areas, the ultrasound apparatus 100 may select a "Frequency" control item for controlling a frequency of an ultrasound signal.

Figure 5:
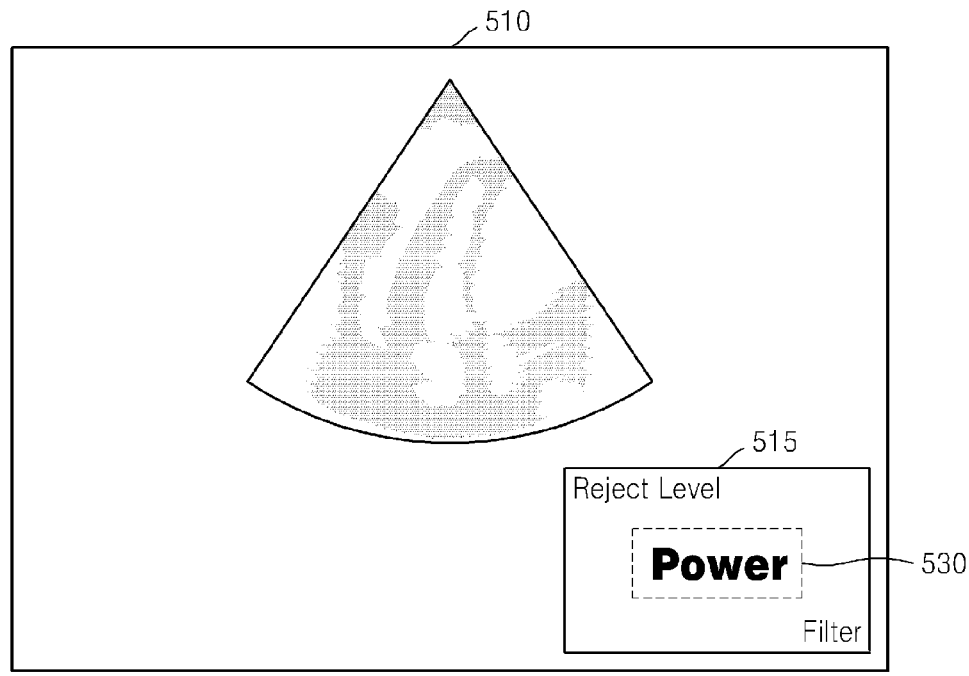
FIG. 5 is a diagram for explaining a method of selecting a control item, according to an embodiment of the present invention.
Figure 5:
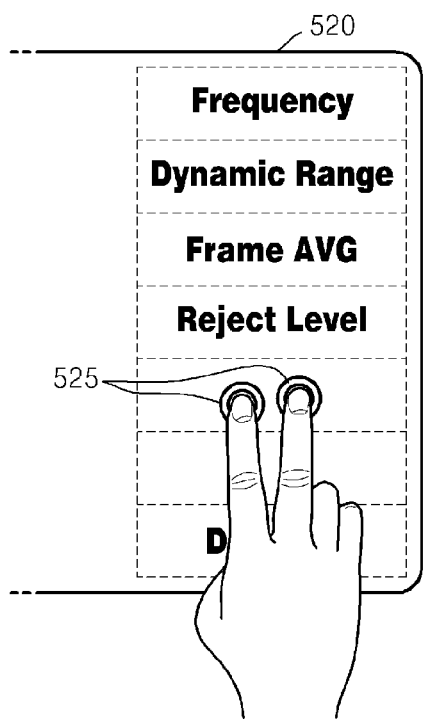

FIG. 5 is a diagram for explaining a method of selecting a control item, according to an embodiment of the present invention. Referring to FIGS. 5 through 9, it is shown that a user input unit and a display unit are implemented separately, for convenience of description. However, the ultrasound apparatus 100 is not limited thereto. An embodiment of the user input unit and the display unit will be described later in FIG. 10.

Referring to FIG. 5, the user input unit 520 detects a touch input to a fifth area from the top among the divided seven control areas. That is, when a user touches the fifth area by using two fingers, the ultrasound apparatus 100 may detect two locations 525 of a touch input and select a "Power" control item which is prematched with the two locations 525.

Then, the ultrasound apparatus 100 displays a control window 515 on a display unit 510. The ultrasound apparatus 100 may display the control window 515 for showing "Power", which is a currently selected control item 530, on the display unit 510.

In FIG. 5, the ultrasound apparatus 100 is illustrated to display the control window 515 on a lower right part of the display unit 510. However, a location of the control window 515 is not limited thereto. For example, the ultrasound apparatus 100 may display the control window 515 at any predetermined location on the display unit 510, and may also display the control window 510 to overlap with an ultrasound image.

The ultrasound apparatus 100 may further display other control items, in addition to the currently selected control item 530 on the control window 515. That is, as illustrated in FIG. 5, the ultrasound apparatus 100 may display "Reject Level" and "Filter" control items together with "Power", which is the currently selected control item 530, via the control window 515. In the current embodiment, the ultrasound apparatus 100 may display one or more control items based on a location of control items arranged in the control area.

Specifically, in a control area shown in a dotted line on the user input unit 520, "Power", which is a fifth control item from the top, is arranged to be next to "Reject Level", which is a fourth control item, and "Filter", which is a sixth control item. The "Filter" control item is not illustrated in FIG. 5. However, the "Filter" control item is arranged in the same way as in FIG. 4. Accordingly, the ultrasound apparatus 100 may display "Reject Level", which is the fourth control item, and "Filter", which is the sixth control item, together with "Power", which is the fifth control item, on the control window 515.

The ultrasound apparatus 100 may display the currently selected control item 530 so that the control item 530 may be visually differentiated from control items which are displayed together. That is, as illustrated in FIG. 5, the ultrasound apparatus 100 may display the currently selected control item 530 on the control window 515 by applying various visual effects, such as thickness, color, a size, or a border, to the control item 530.

Additionally, the ultrasound apparatus 100 may display a location of displayed control items, based on an arrangement order in which the control items match the user input unit 520. That is, the ultrasound apparatus 100 may display the "Reject Level" control item, which is selected when a touch input moves up, on an upper part of the control window 515 and may display the "Filter" control item, which is selected when a touch input moves down, on a lower part of the control window 515.

According to the current embodiment, a user may identify a parameter indicated by a currently selected control item. Additionally, the user may also easily identify a parameter to be selected by changing a location of a touch input. That is, a plurality of control items that match a control area included in the user input unit 520 are not visually displayed on the user input unit 520. Accordingly, the ultrasound apparatus 100 needs to provide the user with information about a control item which is selected according to a location of a touch input. According to the current embodiment, the ultrasound apparatus 100 displays a control item which is currently selected according to a location of a touch input and, at the same time, a control item which is to be selected by moving the location of the touch input. Thus, the ultrasound apparatus 100 may provide the user with a visual guide.

Figure 6:
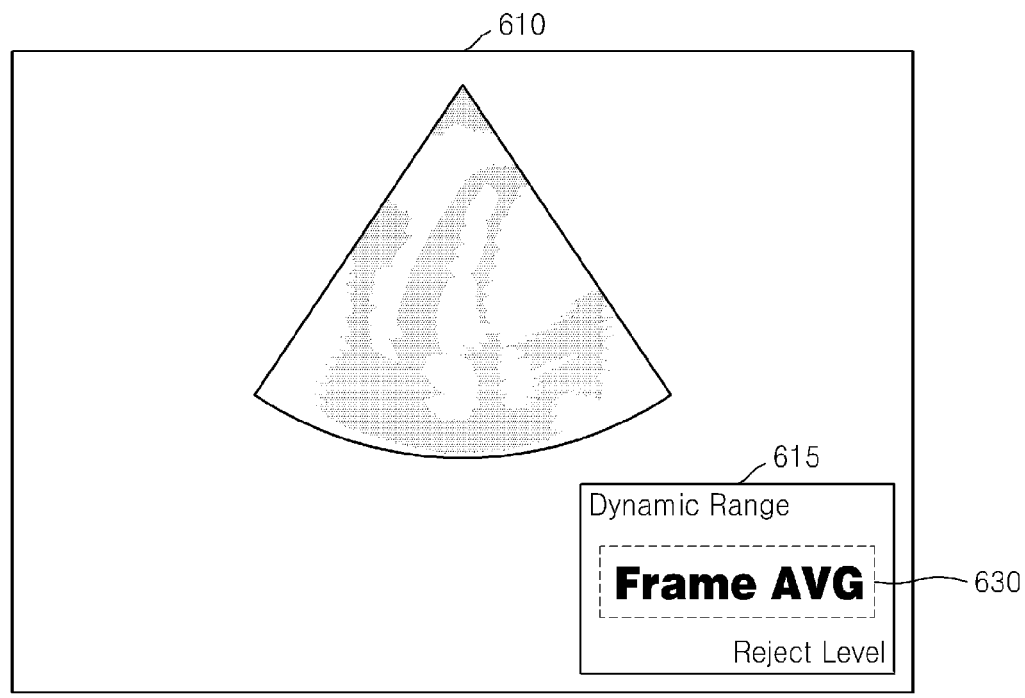
FIG. 6 is a diagram for explaining a method of selecting a control item, according to an embodiment of the present invention.
Figure 6:
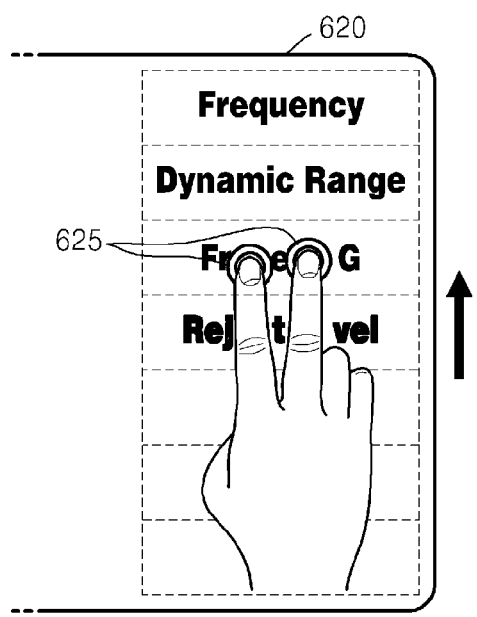

FIG. 6 is a diagram for explaining a method of selecting a control item, according to an embodiment of the present invention. After performing the touch input as shown in FIG. 5, the ultrasound apparatus 100 receives a touch input made by dragging from a fifth control area to a third control area by detecting two locations 625. The third control area of the user input unit 620 matches a "Frame AVG" control item.

Accordingly, the ultrasound apparatus 100 displays the "Frame AVG" control item 630 on the control window 615. Like the description provided with regard to FIG. 5, the ultrasound apparatus 100 may simultaneously display "Dynamic Range" and "Reject Level" control items that match a control area adjacent to the third control area.

Figure 7:
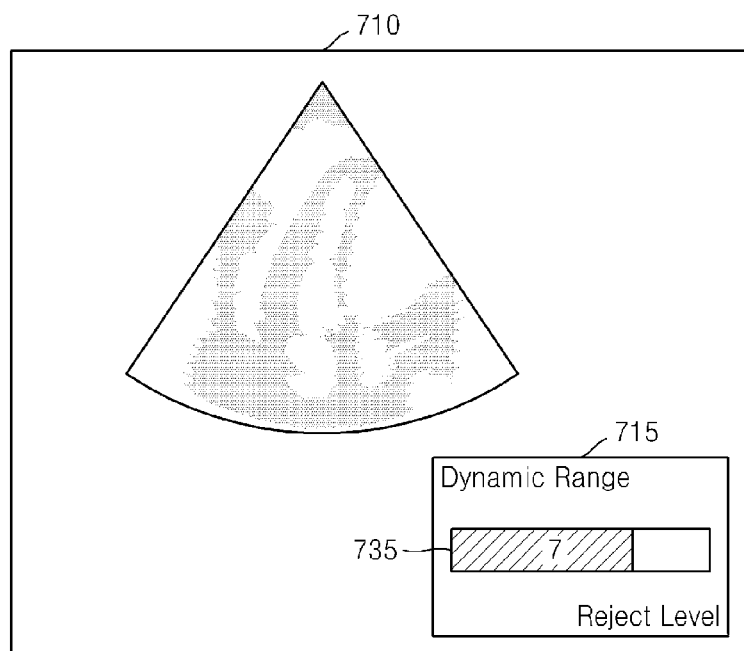
FIG. 7 is a diagram for explaining adjusting of a configuration value, according to an embodiment of the present invention.
Figure 7:
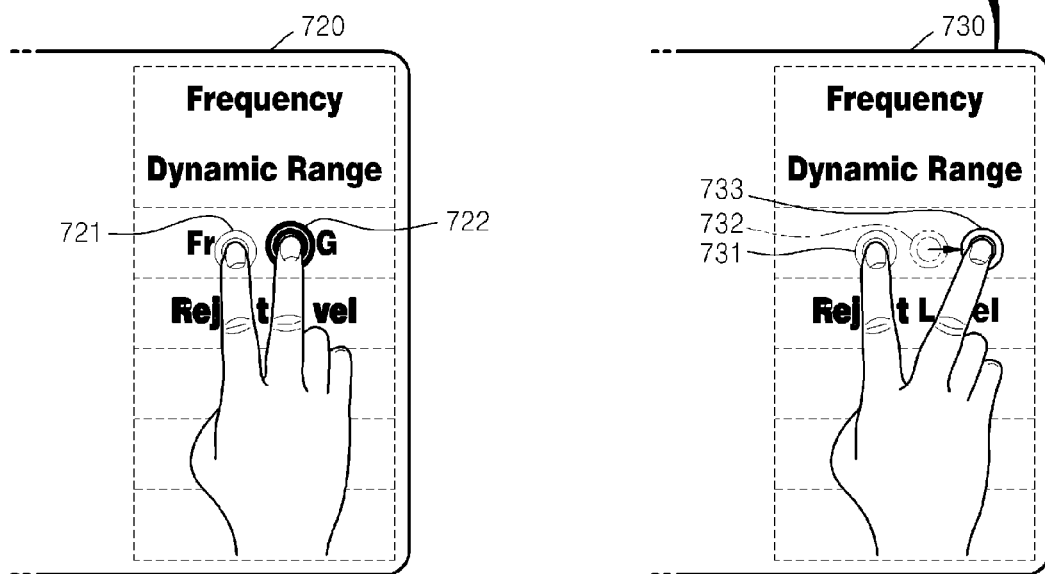

FIG. 7 is a diagram for explaining adjusting of a configuration value, according to an embodiment of the present invention.

After performing the two-point input as shown in FIG. 6, the ultrasound apparatus 100 detects a touch operation regarding a currently selected control item which is "Frame AVG". A lower left part of FIG. 7 shows an embodiment in which a touch operation is a pressure operation. A lower right part of FIG. 7 shows an embodiment in which a touch operation is a location operation.

With regard to the lower left side of FIG. 7, the ultrasound apparatus 100 may detect a change in a pressure of a touch input to a location 722 among two locations 712 and 722. That is, a user may increase a pressure on a right location from among two locations which are touched on the user input unit 720.

The ultrasound apparatus 100 may recognize a pressure operation for increasing a pressure of a touch input as a touch operation for increasing a configuration value. Accordingly, the ultrasound apparatus 100 may increase a configuration value regarding "Frame AVG" which is the currently selected control item.

Then, with regard to an upper part of FIG. 7, the ultrasound apparatus 100 displays a configuration value 735 which is adjusted for a control item which is currently selected on the display unit 710. That is, if the user continues to increase a pressure on the location 722, the ultrasound apparatus 100 may continuously increase a configuration value of "Frame AVG" to 8 through 10.

With regard to a lower right part of FIG. 7, the ultrasound apparatus 100 may detect a change in a location of a touch input regarding a location 732 among two locations 731 and 732. That is, while maintaining a touch input to the location 731, the user may drag a touch input to the location 732 to a right direction.

The ultrasound apparatus 100 may adjust a configuration value of a currently selected control item, according to a direction in which a location of a touch input changes. As illustrated in FIG. 7, if the touch input to the location 732 moves to the right, the ultrasound apparatus 100 may increase a configuration value. Conversely, if the touch input to the location 731 moves to the left, the ultrasound apparatus 100 may decrease a configuration value of the "Frame AVG" control item.

Although not illustrated in FIG. 7, the ultrasound apparatus 100 may also detect a change in two locations of a two-point input. That is, if both the locations 731 and 732 on the lower right part of FIG. 7 move to the right, the ultrasound apparatus 100 may increase a configuration value. If both the locations 731 and 732 move to the left, the ultrasound apparatus 100 may decrease a configuration value.

As another example, the ultrasound apparatus 100 may detect a pinching input and an unpinching input. That is, if a touch input to the location 731 moves to the left and a touch input to the location 732 moves to the right, and thus, an unpinching input by which the two location 731 and 732 become far away from each other is received, the ultrasound apparatus 100 may increase a configuration value. Conversely, if a pinching input by which the two locations 731 and 732 become closer to each other is received, the ultrasound apparatus 100 may decrease a configuration value.

That is, the ultrasound apparatus 100 may pre-match and store various types of touch inputs and a method of adjusting a configuration value. Thus, the ultrasound apparatus 100 may adjust a configuration value of a currently selected control item based on a touch operation of detected touch inputs.

The ultrasound apparatus 100 may also detect an acceleration of a touch operation. That is, if a pressure on the location 722 in a lower left part of FIG. 7 gradually decreases, and then, rapidly increases, the ultrasound apparatus 100 may adjust a configuration value so that the configuration value may be gradually increased, and then, rapidly decreased, based on an acceleration of a pressure change according to a pressure operation.

Likewise, if the location 722 on a lower right part of FIG. 7 rapidly, and then, gradually moves to the location 723, the ultrasound apparatus 100 may adjust a configuration value by reflecting an acceleration when a location changes according to a location operation, so that the configuration value may be rapidly increased, and then, gradually increased. Accordingly, the user may finely or coarsely adjust a configuration value of a control item.

Figure 8:
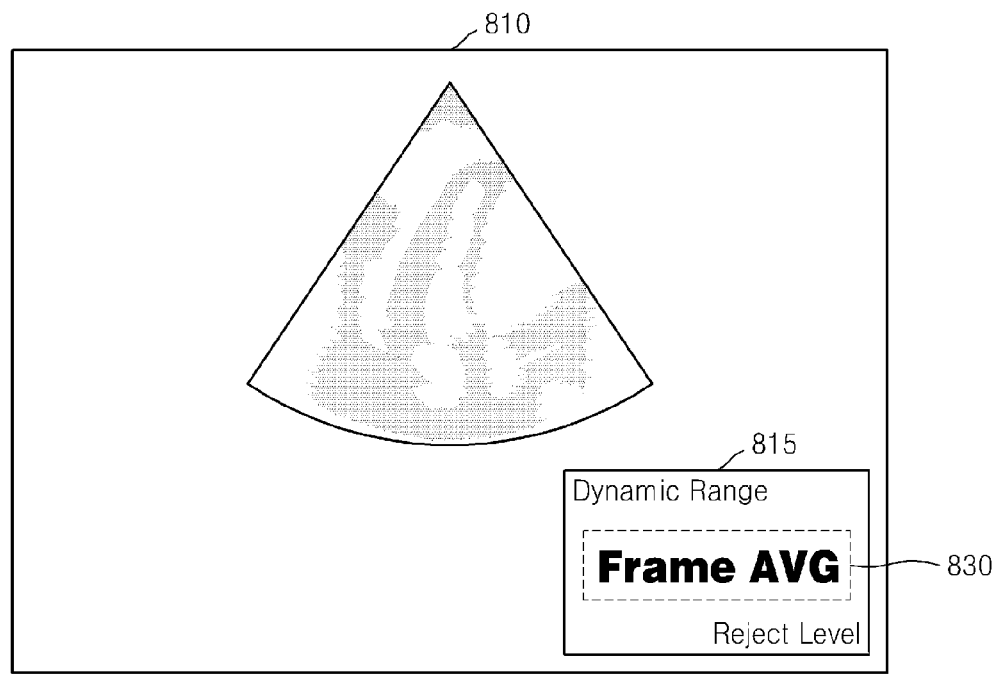
FIG. 8 is a diagram for explaining a control item, according to an embodiment of the present invention.
Figure 8:
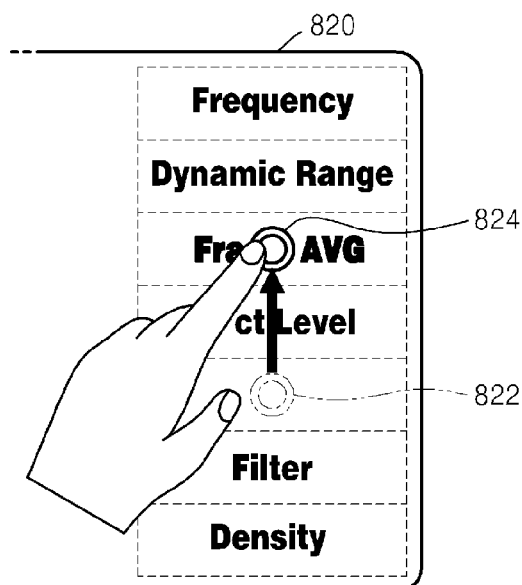

FIG. 8 is a diagram for explaining a control item, according to an embodiment of the present invention. In FIG. 8, the ultrasound apparatus 100 detect a one-point input that is a touch input for dragging from a location 822 of the user input unit 820 to a location 824.

The ultrasound apparatus 100 may select "Frame AVG" which is a control item corresponding to the location 824, and display a control window 815 on a display unit 810, so as to indicate a currently selected control item 830. Like in FIG. 6, according to an order in which a control area is arranged in the user input unit 820, the ultrasound apparatus 100 may display control items arranged next to the currently selected control item 830 in the control window 815.

Figure 9:
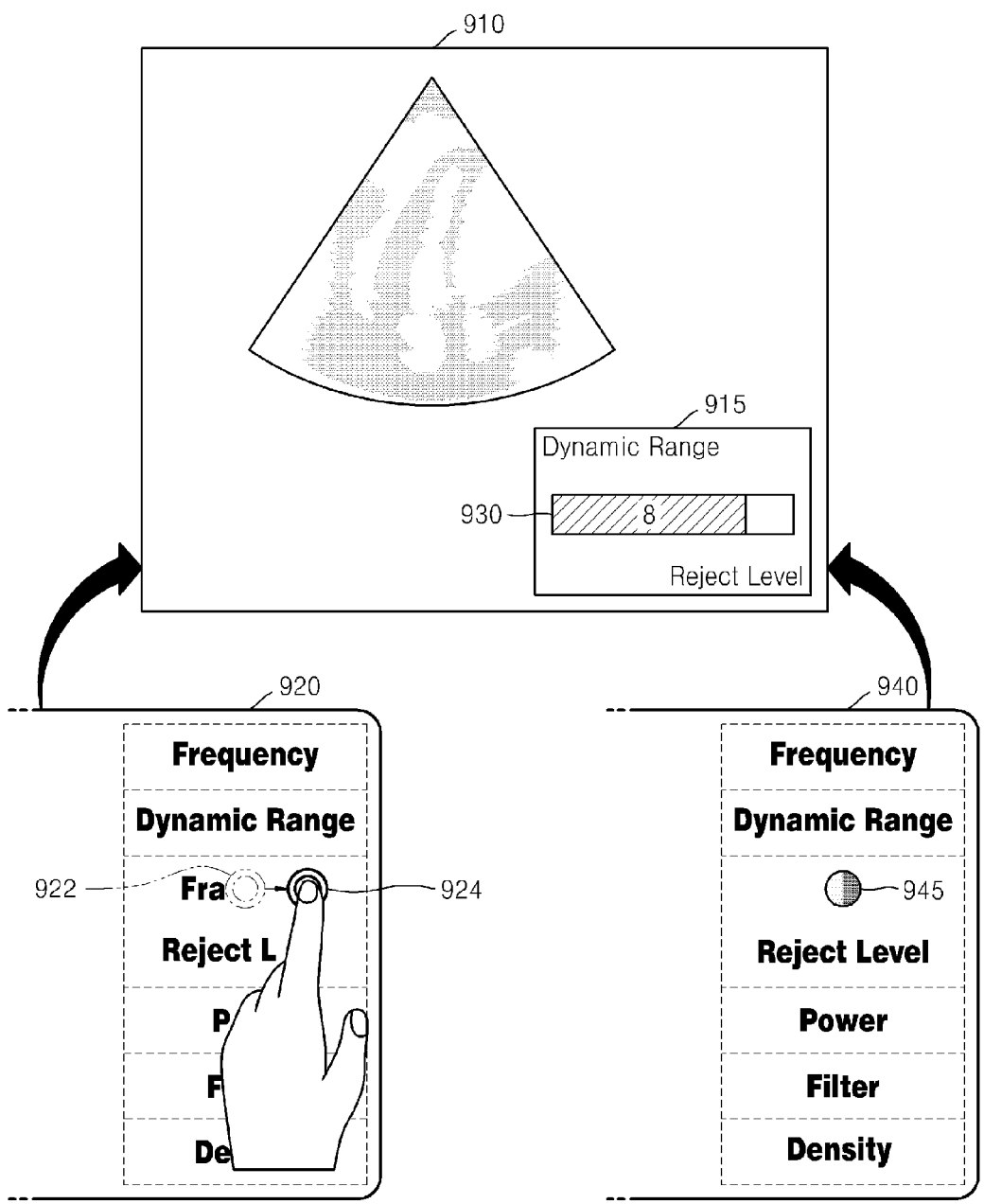
FIG. 9 is a diagram for explaining adjusting of a configuration value, according to an embodiment of the present invention.

FIG. 9 is a diagram for explaining adjusting of a configuration value, according to an embodiment of the present invention. An embodiment, in which a touch operation is a location operation, is shown in a lower left part of FIG. 9. An embodiment, in which a touch operation is a pressure operation, is shown in a lower right part of FIG. 9.

First, a case in which a touch operation is a location operation is described. If a location operation for changing a location 922 to a location 924 is detected, the ultrasound apparatus 100 may increase or decrease a configuration value according to a direction in which a location of a touch input changes. As an example, in FIG. 9, if a location operation for moving a location of a touch input in a right direction is detected, the ultrasound apparatus 100 may increase a configuration value of a currently selected control item. Conversely, if a location of a touch input moves to the left, the ultrasound apparatus 100 may decrease a configuration value.

Additionally, the ultrasound apparatus 100 may adjust a configuration value according to a touch operation for changing a touch input, and display an adjusted configuration value 930 on a control window 915. Thus, a user may immediately identify a change in a configuration value of the currently selected control item.

Then, a case in which a touch operation is a location operation is described. If a pressure of a detected touch input is changed, the ultrasound apparatus 100 may adjust a configuration value according to a direction in which the pressure is changed. As an example, in FIG. 9, with regard to a location 945, the ultrasound apparatus 100 may receive a tilting input made by tilting a touch input to a right direction. In other words, the ultrasound apparatus 100 may detect an increase in a pressure on a right part, which is shown in a dark color, according to a one-point input to the location 945. Accordingly, the ultrasound apparatus 100 may adjust a configuration value of a currently selected control item by increasing the configuration value. The ultrasound apparatus 100 may display the adjusted configuration value 930 for the control item on the control window 950.

In the above description, the ultrasound apparatus 100 receives a touch input for adjusting a configuration value of a control item via the user input unit. However, the ultrasound apparatus 100 may also adjust a configuration value according to a user input which is detected via a display unit. That is, the ultrasound apparatus 100 may receive an input for adjusting a configuration value via at least one of the user input unit and the display unit.

That is, as an example, in FIG. 9, the ultrasound apparatus 100 may receive a drag input via the control window 915 of the display unit 910, instead of receiving a drag input of moving from a location 922 to a location 924 on the user input unit 920. That is, after "Frame AVG" is selected as a control item, and if a touch input of dragging a location on the display unit 910, for example, a location on the control window 915 in a right direction is received from a user, the ultrasound apparatus 100 may increase a configuration value of the "Frame AVG" control item.

Figure 10:
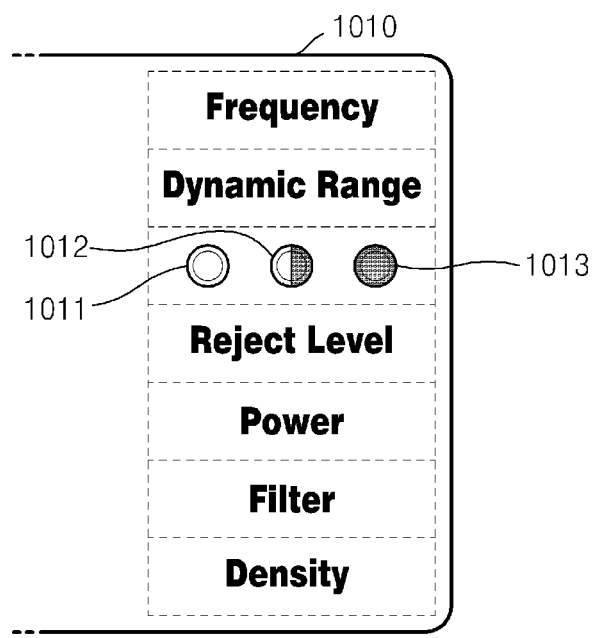
FIG. 10 is a diagram for explaining a pressure operation according to an embodiment of the present invention.

FIG. 10 is a diagram for explaining a pressure operation according to an embodiment of the present invention. As described with regard to FIG. 9, a pressure operation may mean a touch operation for changing a pressure of a touch input. A pressure operation for a one-point input was described by referring to FIG. 9, and a pressure operation for a two-point input was described by referring to FIG. 7.

The ultrasound apparatus 100 may detect a direction in which a pressure of a touch input increases, to adjust a configuration value. In other words, the ultrasound apparatus 100 detects a three-point input of touching locations 1011 through 1013 which are three locations in a user input unit 1010, and then, detects a pressure operation for changing a pressure of the three-point input. For example, if a pressure on the location 1013, from among the three locations 1011 through 1013 of the touch input, increases, the ultrasound apparatus 100 may increase a configuration value. Conversely, if a pressure on the location 1011 increases, the ultrasound apparatus 100 may decrease a configuration value. This may be also applied to a four-point input.

When detecting a pressure operation, the ultrasound apparatus 100 may determine a direction in which a pressure increases/decreases with reference to a center of a touch input. In other words, the ultrasound apparatus 100 may determine a center of a touch input of touching the user input unit 1010, and determine a direction of a pressure change by comparing a location in which a pressure changes to the center of the touch input.

As an example, in FIG. 10, the ultrasound apparatus 100 may determine a direction of a pressure change, with reference to a center point of a touch input of touching the location 1012 of the user input 1010. The ultrasound apparatus 100 may determine that, if a pressure on a part that is shown in black, a pressure increases in a right direction and, if a pressure on a part that is shown in white increases, a pressure increases in a left direction.

Figure 11:
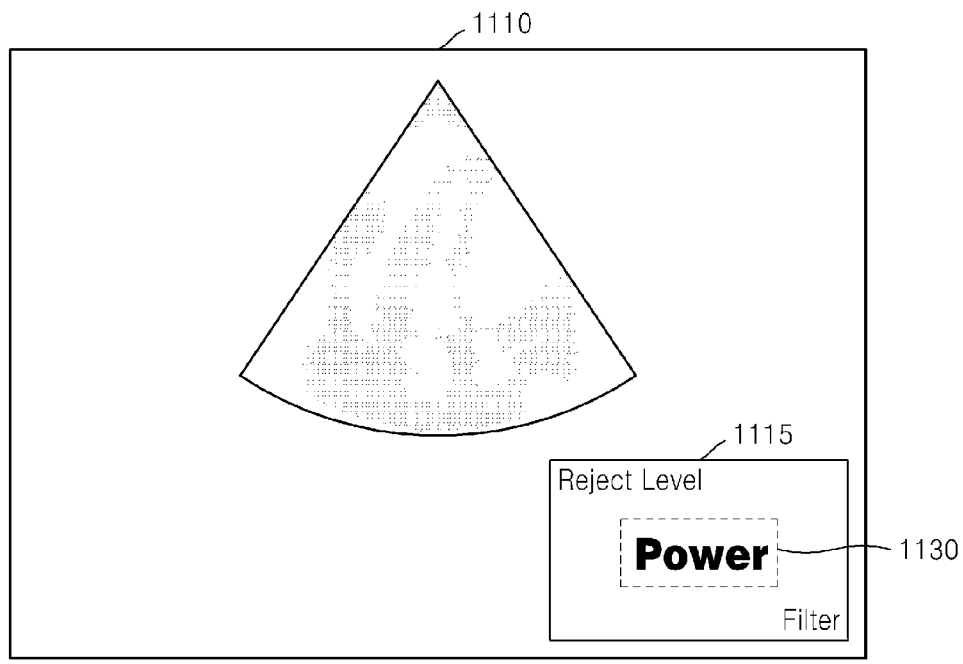
FIG. 11 is a diagram illustrating a control item that is arranged in a horizontal direction according to an embodiment of the present invention.
Figure 11:
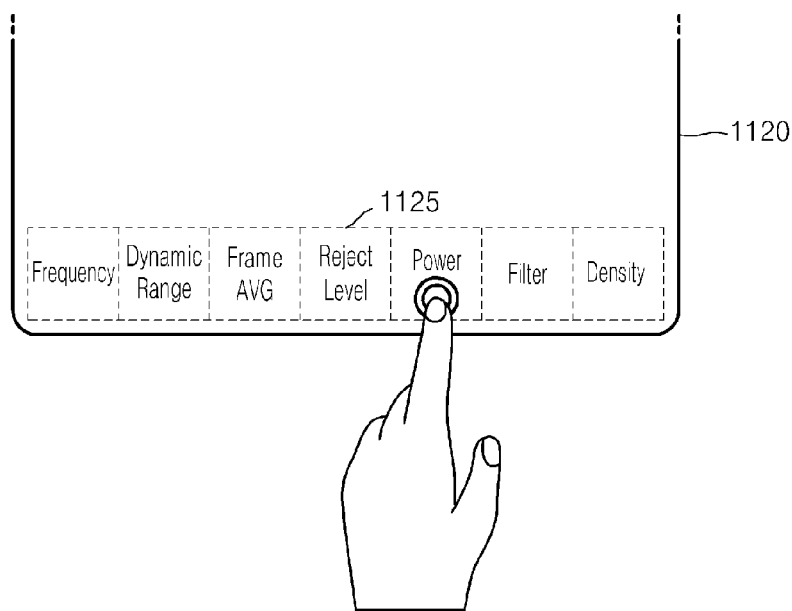

FIG. 11 is a diagram illustrating a control item that is arranged in a horizontal direction according to an embodiment of the present invention. As described with regard to FIG. 4, a plurality of parameters that are included in a control item respectively match a plurality of areas that are located in the control area 1125. Differently from FIG. 4, FIG. 11 shows an embodiment in which seven parameters are arranged in a horizontal direction.

If a user touches a location that corresponds to a "Power" parameter in the control area 1125 of the user input unit 1120, the ultrasound apparatus 100 displays a control window 1115 that shows a currently selected control item 1130.

Figure 12:
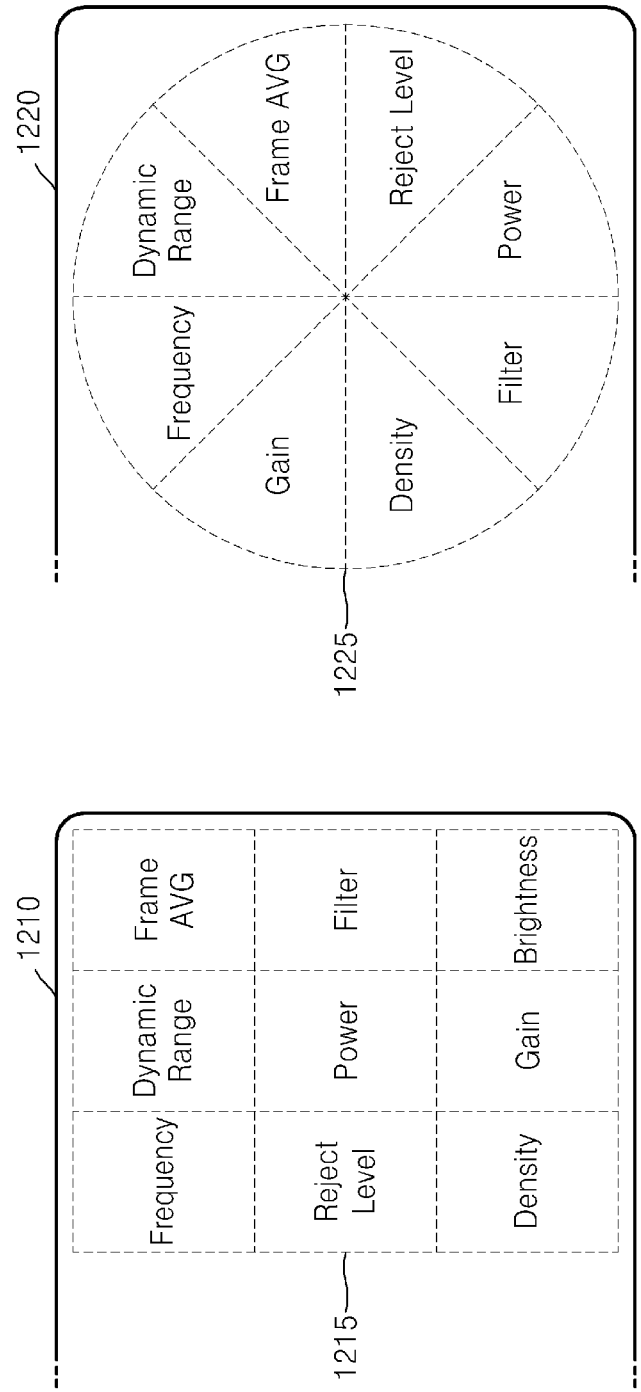
FIG. 12 is a diagram illustrating a control item that is arranged in a grid pattern and in a circle pattern according to an embodiment of the present invention.

FIG. 12 is a diagram illustrating control items that are arranged respectively in a grid pattern and in a circle pattern according to an embodiment of the present invention. On a left side of FIG. 12, a control item that is arranged in a grid pattern is displayed in a control area 1215 of a user input unit 1210. On a right side of FIG. 12, a control item that is arranged in a circle pattern is displayed in a control area 1225 of a user input unit 1220.

As described above, a control item may be arranged on a user input unit in various patterns by using various methods.

An arrangement of a control item is not limited to the embodiments shown in FIGS. 4, 11, and 12.

Figure 13:
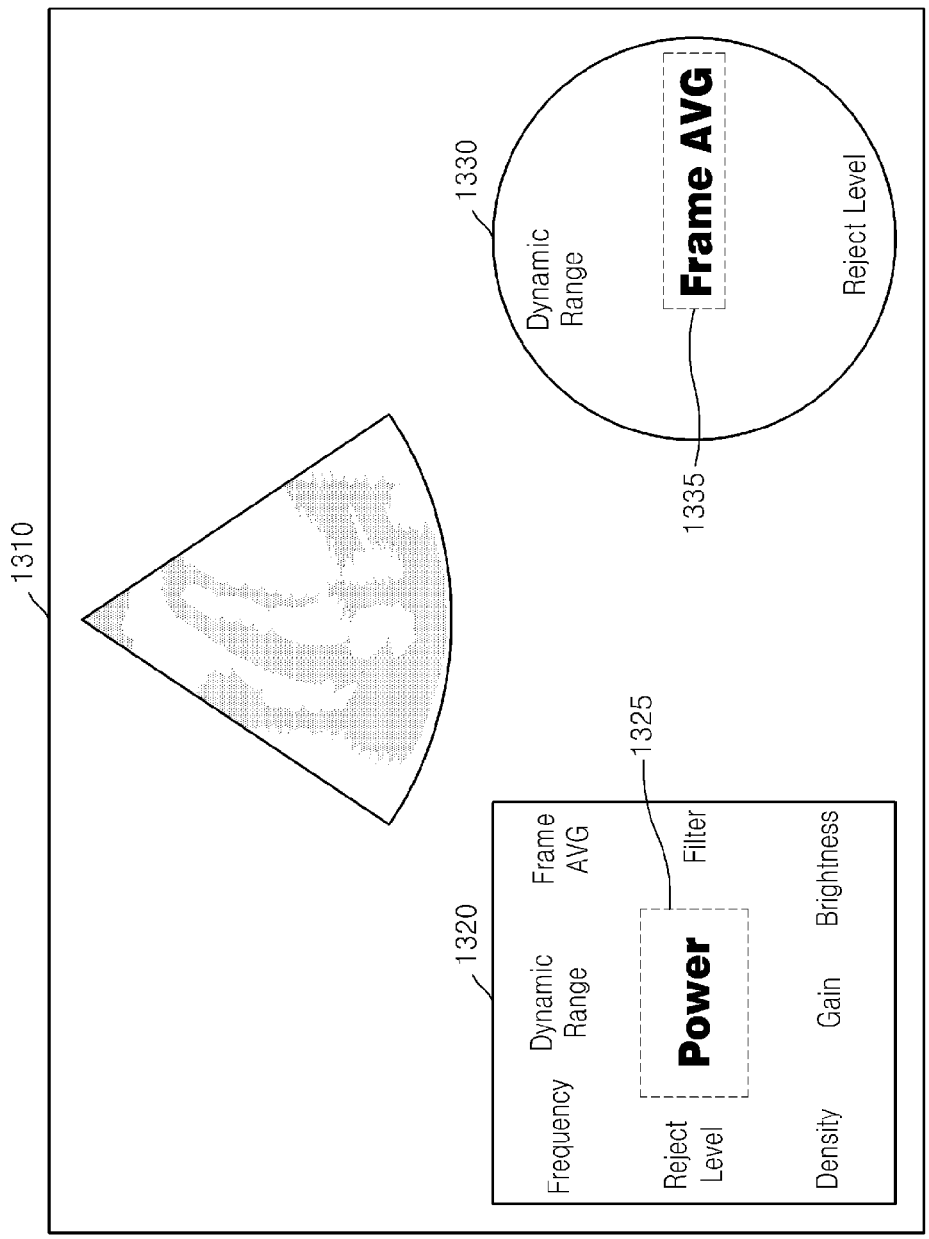
FIG. 13 is a diagram illustrating a control window according to an embodiment of the present invention.

FIG. 13 is a diagram illustrating control windows 1320 and 1330 according to an embodiment of the present invention. The ultrasound apparatus 100 may display the control window 1320 for a control item that is arranged in a grid pattern or the control window 1330 for a control item that is arranged in a circle pattern on a display unit 1310. Locations of the control window 1320, displayed on a lower left side of the display unit 1310, and the control window 1330, displayed on a lower right side of the display unit 1310, are only examples that are provided for convenience of description, and are not limited thereto.

If a control item is arranged in a grid pattern, and a currently selected control item is "Power", the ultrasound apparatus 100 may display eight control items, which are arranged adjacent to a "Power" control item 1325, together with the "Power" control item 1325 on the control window 1320. Likewise, if a control item is arranged in a circle pattern and a currently selected control item is "Frame AVG", the ultrasound apparatus 100 may display two control items, which are arranged adjacent to a "Frame AVG" control item 1335 in a circle, together with the "Frame AVG" control item 1335 on the control window 1330.

As described in detail with regard to FIG. 13, the ultrasound apparatus 100 may display a control item, which is arranged adjacent to a currently selected control item, together with the selected control item on a control window. The ultrasound apparatus 100 may display one or more control items on the control window. based on a pattern and an order in which the control items are arranged in the control area.

Figure 14:
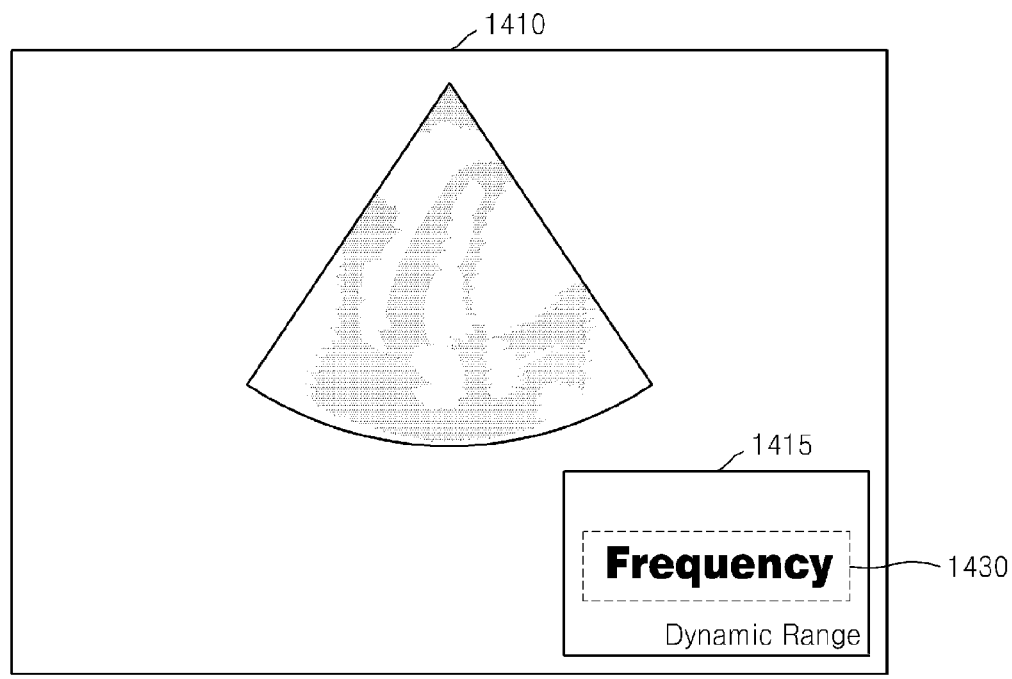
FIG. 14 is a diagram for explaining a selection of a control item that is placed in a predetermined location, according to an embodiment of the present invention.
Figure 14:
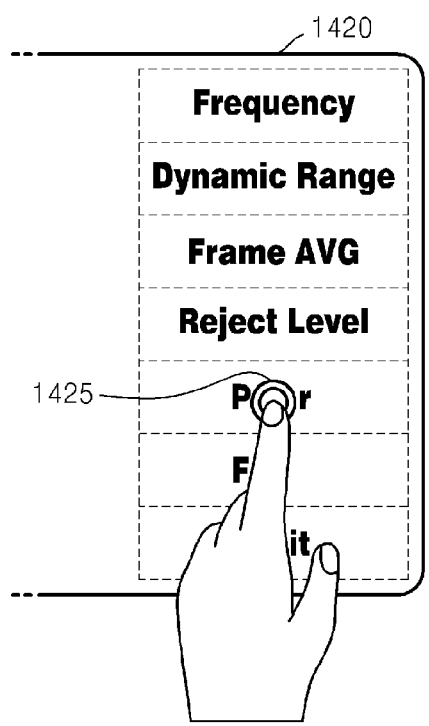

FIG. 14 is a diagram for explaining a selection of a control item that is placed in a predetermined location, according to an embodiment of the present invention. As described in detail with regard to FIG. 3, the ultrasound apparatus 100 may select a control item that corresponds to a predetermined location, as well as a control item that corresponds to a location of a detected touch input.

According to an embodiment of the present invention, in operation S310, the ultrasound apparatus 100 may obtain a control item that corresponds to a predetermined location. In other words, the ultrasound apparatus 100 may obtain a control item that corresponds to a location, which is pre-stored in the ultrasound apparatus 100, regardless of a location of a touch input in a control area.

As an example, in FIG. 14, the ultrasound apparatus 100 detects a user input of touching a location 1425 of the user input unit 1420, which corresponds to a "Power" control item. According to an embodiment of the present invention, however, the ultrasound apparatus 100 may select a "Frequency" control item, instead of the control item "Power" that corresponds to the location 1425 of the touch input. The ultrasound apparatus 100 may display the selected "Frequency" control item 1430 on a control window 1415 of the display unit 1410.

In other words, if the "Frequency" control item 1430 is selected at a relatively high frequency compared to other control items, when a touch input is detected, the ultrasound apparatus 100 may select the "Frequency" control item 1430 regardless of a location in which the touch input is detected. Alternately, a user of the ultrasound apparatus 100 may directly select a control item that is to be selected first.

Accordingly, the user of the ultrasound apparatus 100 may be provided with an opportunity for quickly selecting a desired control item. In other words, regardless of whichever location of a control area that is included in the user input unit 1420 is touched by the user, the ultrasound apparatus 100 may obtain a predetermined control item "Frequency" 1430.

Then, if the user drags a one-point input to the location 1425 in a downward direction, and thus, touches a location that corresponds to a "Filter" control item, the ultrasound apparatus 100 may obtain a "Dynamic Range" control item that is arranged below the "Frequency" control item.

FIG. 15 is a diagram for explaining an embodiment in which a touch input is detected via a control window 1515. As described with regard to FIG. 9, the ultrasound apparatus 100 may also receive a touch input of adjusting a configuration value via the control window.

In other words, the ultrasound apparatus 100 may display the control window 1515 on the display unit 1510, and detect a touch input of dragging from a location 1516 to a location 1517, which are located on the control window 1515.

When a touch input on the control window 1515 is detected, the ultrasound apparatus 100 may adjust a configuration value for a currently selected "Frame AVG" control item. In other words, the ultrasound apparatus 100 may increase a configuration value of the "Frame AVG" control item, and display an adjusted configuration value 1520 on the control window 1515.

FIGS. 16A through 16C are diagrams for explaining several methods of receiving a touch input, according to an embodiment of the present invention. As described above, in FIGS. 5 through 15, it is shown that a user input unit and a display unit are implemented separately, for convenience of description. However, the ultrasound apparatus 100 is not limited thereto.

That is, as illustrated in FIG. 16A, the ultrasound apparatus 100 may receive a touch input from a user via a user input unit 1615 which is provided on the control panel, separately from a display unit 1610 for displaying an ultrasound image.

Additionally, as illustrated in FIG. 16B, if a display unit 1620 for displaying an ultrasound image is a touch screen, the ultrasound apparatus 100 may receive a touch input of a user via the display unit 1620. That is, the display unit 1620 may function as a user input unit.

Otherwise, as illustrated in FIG. 16C, the ultrasound apparatus 100 may be implemented as a mobile terminal. For example, the ultrasound apparatus 100 may be implemented as a mobile terminal of various types such as a PACS viewer, a cellular phone, a smart phone, a laptop computer, a tablet PC, or the like. A display unit 1630 of the ultrasound apparatus 100, illustrated in FIG. 16C, may function as a user input unit, similarly to the embodiment illustrated in FIG. 16B. That is, the display unit 1630 of the ultrasound apparatus 100 may be an input element for detecting a touch input of a user.

Embodiments of the ultrasound apparatus 100 are not limited to the descriptions with regard to FIGS. 16A through 16C. The ultrasound apparatus 100 may display an ultrasound image and receive a user input by using other various methods.

As described above, according to the one or more of the above embodiments of the present invention, a user of the ultrasound apparatus may easily adjust a parameter of the ultrasound apparatus via a user input unit, without having to identify a location of a hardware device. Accordingly, the user may manipulate the ultrasound apparatus 100 while looking at an ultrasound image of an object, and identify a result of the manipulation. Thus, time for diagnosing an object may be shortened and image accuracy may also be improved.

In addition, other embodiments of the present invention can also be implemented through computer readable code/instructions in/on a medium, e.g., a computer readable medium, to control at least one processing element to implement any above described embodiment. The medium can correspond to any medium/media permitting the storage and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more embodiments of the present invention. The media may also be a distributed network, so that the computer readable code is stored/transferred and executed in a distributed fashion. Furthermore, the processing element could include a processor or a computer processor, and processing elements may be distributed and/or included in a single device.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of inputting information into an ultrasound apparatus that comprises an input which receives a touch input, the method comprising:
   receiving a user input for selecting one of a plurality of areas of a control area of the input;
   selecting a control item of the ultrasound apparatus corresponding to the one area selected by the user input;
   displaying a control window for displaying the selected control item on a screen separate from the input; and
   adjusting a configuration value of the selected control item based on a touch operation of a two-point touch input that touches two locations of the one area,
   wherein the adjusting the configuration value comprises adjusting the configuration value of the selected control item based on a difference in a pressure applied on the two locations of the one area by the two-point touch input or a direction in which the two locations of the one area are changed by the two-point touch input.

2. The method of claim 1, wherein the control item comprises a plurality of parameters regarding an ultrasound image, and
   wherein the plurality of parameters match the plurality of areas which are arranged in the control area.

3. The method of claim 2, wherein the displaying of the control window comprises displaying the selected control item and another control item that is arranged adjacent to the selected control item in the control window.

4. The method of claim 2, wherein the plurality of areas are arranged in at least one from among a horizontal direction of the control area, a vertical direction of the control area, a circle pattern, and a grid pattern.

5. The method of claim 1, wherein the receiving of the user input and the selecting of the control item comprise:
   detecting a location of a touch input to the control area of the user; and
   obtaining the control item which corresponds to the detected location.

6. The method of claim 1, further comprising displaying the adjusted configuration value in the control window.

7. The method of claim 1, wherein, when the touch operation comprises the pressure operation, the adjusting of the configuration value comprises increasing or decreasing the configuration value in a direction in which a pressure of the touch input to the control area increases.

8. The method of claim 7, wherein the direction in which the pressure increases is determined based on a center of the touch input.

9. The method of claim 1, wherein, when the touch operation increases the location operation, the adjusting of the configuration value comprises increasing or decreasing the configuration value in a direction in which a location of the touch input to the control area is changed.

10. The method of claim 9, wherein the direction in which the location is changed is a direction in which the touch input is dragged.

11. The method of claim 1, wherein the receiving of the user input and the selecting of the control item comprise:
    detecting a touch input of the user to the control area; and
    obtaining the control item that corresponds to a predetermined location in the control area.

12. The method of claim 11, wherein the predetermined location is determined based on at least one of a frequency in which the control item is selected and the user input.

13. The method of claim 1, wherein the adjusting comprises adjusting the configuration value based on acceleration of the touch input for changing the touch input.

14. The method of claim 1, wherein the control item comprises at least one parameter from among a frequency of an ultrasound signal, a dynamic range, a frame average, a reject level, a power, a filter, and a line density, the parameter being related to an operation of the ultrasound apparatus.

15. The method of claim 1, wherein the control item comprises at least one parameter from among color, brightness, a chroma, sharpness, contrast, and resolution, the parameter being related to an image output of the ultrasound apparatus.

16. The method of claim 1, wherein the input is one of a touch screen, a touch panel, and a touch pad.

17. An ultrasound apparatus comprising:
    an obtainer for obtaining ultrasound data from an object;
    an input that comprises a control area including a plurality of areas and receives a selection of one of the plurality of areas corresponding to a selection of a control item of the ultrasound apparatus;
    a display, separate from the input, for displaying an ultrasound image based on the ultrasound data, and displaying a control window which shows the selected control item; and
    a controller for adjusting a configuration value of the selected control item based on a touch operation of a two-point touch input that touches two locations of the one area,
    wherein the controller adjusts the configuration value of the selected control item based on a difference in a pressure applied on the two locations of the one area by the two-point input or a direction in which the two locations of the one area are changed by the two-point input.

18. The ultrasound apparatus of claim 17, wherein the control item comprises a plurality of parameters regarding an ultrasound image, and
wherein the plurality of parameters match the plurality of areas which are arranged in the control area.

19. The ultrasound apparatus of claim 18, wherein the display displays the selected control item and another control item that is arranged adjacent to the selected control item in the control window.

20. The ultrasound apparatus of claim 18, wherein the plurality of areas are arranged in at least one from among a horizontal direction of the control area, a vertical direction of the control area, a circle pattern, and a grid pattern.

21. The ultrasound apparatus of claim 17, wherein the input detects a location of a touch input to the control area of the user and obtains the control item which corresponds to the detected location.

22. The ultrasound apparatus of claim 17, wherein the display displays the adjusted configuration value on the control window.

23. The ultrasound apparatus of claim 17, wherein, when the touch operation comprises the pressure operation, the controller increases or decreases the configuration value in a direction in which a pressure of the touch input to the control area increases.

24. The ultrasound apparatus of claim 23, wherein the direction in which the pressure increases is determined based on a center of the touch input.

25. The ultrasound apparatus of claim 17, wherein, when the touch operation increases the location operation, the controller increases or decreases the configuration value in a direction in which a location of the touch input to the control area is changed.

26. The ultrasound apparatus of claim 25, wherein the direction in which the location is changed is a direction in which the touch input is dragged.

27. The ultrasound apparatus of claim 17, wherein the input detects a touch input of the user to the control area, and obtains the control item that corresponds to a predetermined location in the control area.

28. The ultrasound apparatus of claim 27, wherein the predetermined location is determined based on at least one of a frequency in which the control item is selected, and a user input.

29. The ultrasound apparatus of claim 17, wherein the controller adjusts the configuration value based on acceleration of the touch input for changing the touch input.

30. The ultrasound apparatus of claim 17, wherein the control item comprises at least one parameter such as a frequency of an ultrasound signal, a dynamic range, a frame average, a reject level, a power, a filter, and a line density, the parameter being related to an operation of the ultrasound apparatus.

31. The ultrasound apparatus of claim 17, wherein the control item comprises at least one parameter such as color, brightness, a chroma, sharpness, contrast, and resolution, the parameter being related to an image output of the ultrasound apparatus.

32. The ultrasound apparatus of claim 17, wherein the input is one of a touch screen, a touch panel, and a touch pad.

33. A non-transitory computer-readable storage medium having stored thereon a computer program, which when executed by a computer, performs the method of claim 1.

* * * * *